United States Patent
Iwamoto et al.

(10) Patent No.: US 7,157,713 B2
(45) Date of Patent: Jan. 2, 2007

(54) DEVICE AND METHOD FOR IDENTIFYING PLASTIC

(75) Inventors: Hiroshi Iwamoto, Toyonaka (JP); Takao Hisazumi, Ibaraki (JP); Yuji Maniwa, Nagaokakyo (JP)

(73) Assignee: Matsushita Eco Technology Center Co., Ltd., Hyogo (JP)

( * ) Notice: Subject to any disclaimer, the term of this patent is extended or adjusted under 35 U.S.C. 154(b) by 357 days.

(21) Appl. No.: 10/250,893

(22) PCT Filed: Oct. 28, 2002

(86) PCT No.: PCT/JP02/11171

§ 371 (c)(1),
(2), (4) Date: Jul. 9, 2003

(87) PCT Pub. No.: WO03/038412

PCT Pub. Date: May 8, 2003

(65) Prior Publication Data

US 2004/0069947 A1    Apr. 15, 2004

(30) Foreign Application Priority Data

Oct. 29, 2001  (JP)  ............................ 2001-330445

(51) Int. Cl.
*G01J 5/02* (2006.01)

(52) U.S. Cl. ............................................. 250/339.12

(58) Field of Classification Search ............ 250/339.12
See application file for complete search history.

(56) References Cited

U.S. PATENT DOCUMENTS

| | | | |
|---|---|---|---|
| 4,636,435 A | | 1/1987 | Yanagihara et al. |
| 4,890,577 A | * | 1/1990 | Maibach .................... 119/52.1 |
| 4,980,454 A | | 12/1990 | Tamai et al. |
| 5,091,647 A | * | 2/1992 | Carduner et al. ...... 250/339.09 |
| 5,216,244 A | | 6/1993 | Esaki et al. |
| 5,510,619 A | * | 4/1996 | Zachmann et al. .... 250/339.08 |
| 5,512,752 A | | 4/1996 | Aikawa et al. |
| 5,777,330 A | | 7/1998 | Murase et al. |
| 6,108,077 A | * | 8/2000 | Heaton et al. ............... 356/213 |
| 6,335,376 B1 | * | 1/2002 | Allen et al. ................. 521/40.5 |
| 6,518,572 B1 | | 2/2003 | Kishii et al. |
| 6,563,119 B1 | | 5/2003 | Zoidis |
| 6,610,981 B1 | * | 8/2003 | Sommer, Jr. ........... 250/339.06 |
| 6,845,869 B1 | * | 1/2005 | Graf von Deym et al. . 209/522 |
| 6,852,977 B1 | * | 2/2005 | Hisazumi et al. ...... 250/339.12 |

FOREIGN PATENT DOCUMENTS

| | | |
|---|---|---|
| DE | 195 02 134 | 8/1996 |
| EP | 1 286 153 | 2/2003 |

(Continued)

*Primary Examiner*—David Porta
*Assistant Examiner*—Christine Sung
(74) *Attorney, Agent, or Firm*—Hamre, Schumann, Mueller & Larson, P.C.

(57) ABSTRACT

A plastic identifying apparatus of the present invention is provided with a sampling unit (2) that samples a test piece (1) from an item to be identified that contains plastic; an identifying unit (3) provided with a detection unit (4) that identifies a type of plastic contained in the test piece (1); and a supply unit (5) that supplies the test piece (1) from the sampling unit (2) to the detection unit (4). With this plastic identifying apparatus, it is possible to realize a plastic identifying method of the present invention, and to identify the types of plastics contained in items to be identified with good accuracy, and continuously, regardless of the size of the items.

16 Claims, 13 Drawing Sheets

FOREIGN PATENT DOCUMENTS

| | | |
|---|---|---|
| JP | 64-6761 | 1/1989 |
| JP | 5-273122 | 10/1993 |
| JP | 7-239297 | 9/1995 |
| JP | 8-136449 | 5/1996 |
| JP | 10-154734 | 6/1998 |
| JP | 11211634 A * | 8/1999 |
| JP | 2000-186987 | 7/2000 |
| JP | 2000-199734 | 7/2000 |
| JP | 2000-214084 | 8/2000 |
| JP | 2001-122978 | 5/2001 |
| JP | 2001-194297 | 7/2001 |
| JP | 2002286637 A * | 10/2002 |

* cited by examiner

DEVICE AND METHOD FOR IDENTIFYING PLASTIC

TECHNICAL FIELD

The present invention relates to plastic identifying apparatuses and plastic identifying methods.

BACKGROUND ART

Conventionally, waste plastics discarded from households and so on are disposed of by such means as incineration and burying. However, incineration and burying have been increasingly accompanied by an environmental impact, shortages of landfill areas, and other social problems. In recent years, work has progressed concerning the sorting/recovering and recycling of waste plastics, and for these reasons, identifying the types of waste plastics has been seen as extremely important. Also, in order to achieve processing for as much waste plastics as possible, there is a need for such identification to be performed with good accuracy and continuously.

Conventionally, methods of identifying types of waste plastics include methods that involve comparison of specific gravities, and methods using fluorescent X-rays or near-infrared light. However, it has been very difficult up until now to identify plastic types with good accuracy and continuously. For example, when there are almost no differences between the specific gravities of plastics, it is very difficult to use methods that involve weight comparisons. And for identification methods using near-infrared light, it is difficult to identify plastics when, for example, they are dark-colored plastics. However, for household electrical appliances discarded from households, for example, television receivers, there are many dark-colored waste plastics, and there are additional difficulties in identifying these with good accuracy because of such factors as surface coatings on the plastics, surface degradation due to long use, smearing of grime and other dirt, and the flame retardants contained within these products. It should be noted that throughout this specification, near-infrared light refers to the light whose wave number is in the range approximately from 4,000 cm$^{-1}$ to 13,000 cm$^{-1}$.

Furthermore, conventionally, identification is performed directly for household electrical appliances such as, for example, television receiver chassis. However, in recent years, the size of television receivers has been increasing, and the sizes of the discarded chassis also have been increasing. In terms of the tasks and labor required, it is difficult to directly identify these types of large-sized plastic products. Also, they make it difficult to introduce continuous lines at recycling plants and inevitably involve increasing the size of the equipment required for identification.

DISCLOSURE OF INVENTION

In view of such conditions, it is an object of the present invention to provide a plastic identifying apparatus and plastic identifying method that enable plastic types to be identified accurately and continuously, regardless of the size of the plastic-containing items to be identified.

To achieve this object, a plastic identifying apparatus of the present invention is provided with a sampling unit that samples a test piece of the item to be identified that contains plastic, and an identifying unit provided with a detection unit that identifies types of plastics, including the above-mentioned test piece, as well as a supply unit to supply the test piece from the sampling unit to the detection unit.

The detection unit of the plastic identifying apparatus is also capable of irradiating infrared light of a predetermined wave number onto the test piece, and detecting the intensity of the infrared light that is totally reflected by the test pieces.

The plastic identifying apparatus also can be provided with a pressing device that brings the test piece into contact with the detection unit.

The plastic identifying apparatus also can be provided with a cleaning unit that cleans the detection unit.

The sampling unit of the plastic identifying apparatus also can be provided with a means for punching a test piece from the item to be identified.

It is possible for the punching means of the plastic identifying apparatus to be a punch press.

The plastic identifying apparatus also can be provided with a chucking unit that holds the test piece sampled by the sampling unit.

The chucking unit of the plastic identifying apparatus also can be provided with a rotation unit that rotates the test piece around a horizontal rotational axis while the chucking unit holds the test piece.

The test piece of the plastic identifying apparatus can be in the form of an approximate "T", shape, or in the form of an approximate "L" shape.

The detection unit of the plastic identifying apparatus can perform identification for at least two surfaces of the test piece.

The plastic identifying apparatus also can be provided with a cleaning unit that surface cleans the test piece.

The plastic identifying apparatus also can be provided with a pressing unit that presses against a surface of the test piece.

The plastic identifying apparatus also can be provided with a polishing unit that provides a surface of the test piece with uniformity.

The plastic identifying method of the present invention includes:

(i) a step of sampling a test piece from an item to be identified that contain plastics, (ii) a step of supplying the sampled test piece to a detection unit for identification of the type of plastic contained in the test piece, and (iii) a step of identifying the type of plastic contained in the test piece with the detection unit.

In the plastic identifying method, step (ii) can contain a step of irradiating infrared light of a predetermined wave number onto the item to be identified, and the intensity of the infrared light totally reflected by these items is detected.

In the plastic identifying method, step (iii) can be performed by bringing the test piece into contact with the detection unit.

In the plastic identifying method, step (iii) can be performed by bringing the test piece into contact with the detection unit after letting the test piece become stationary above the detection unit.

In the plastic identifying method, step iii) can be performed for at least two surfaces of the test piece.

BEST MODE FOR CARRYING OUT THE INVENTION

Figure 1:
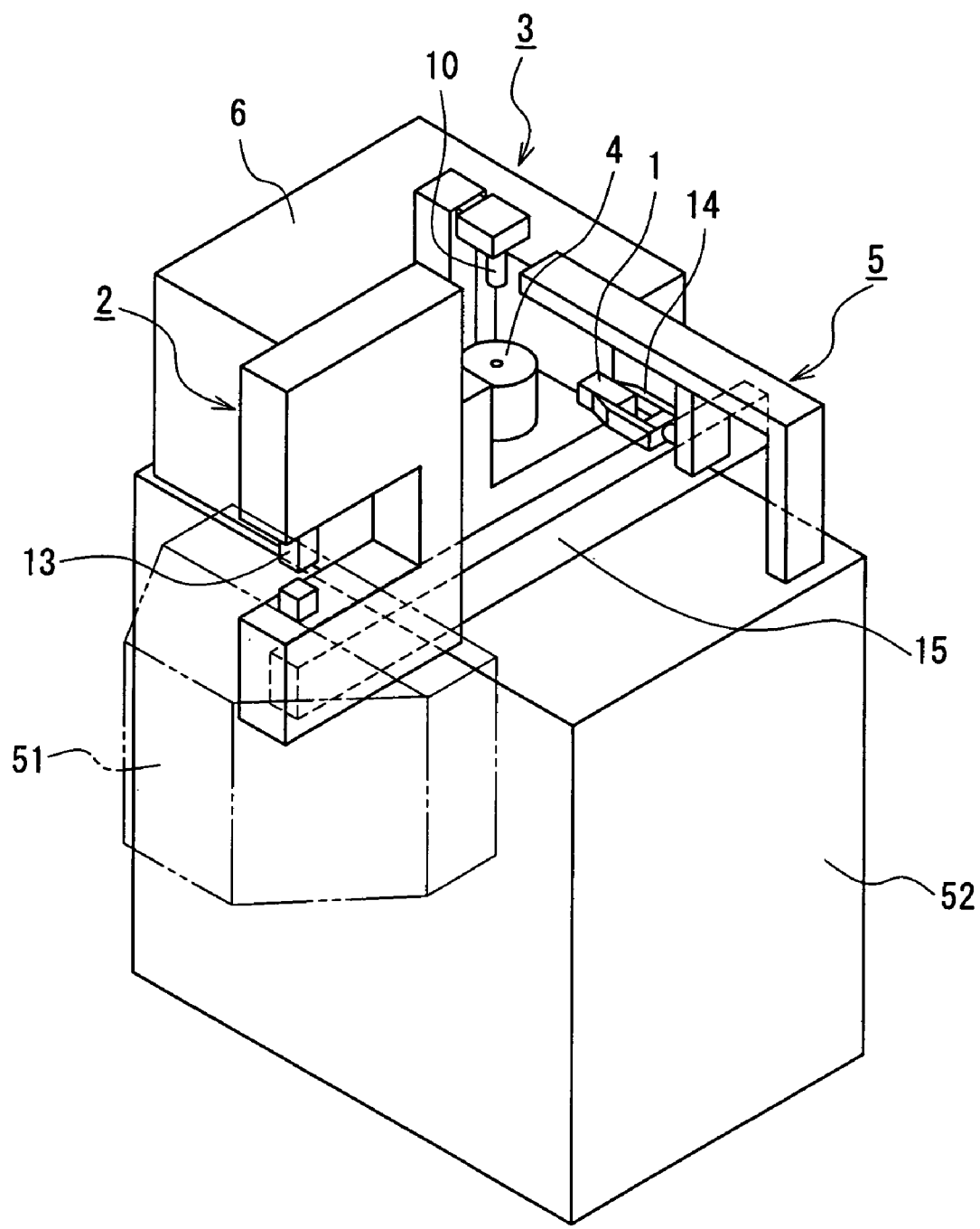
FIG. 1 is a schematic drawing showing an example of a plastic identifying apparatus of the present invention.

Referring to the accompanying drawings, the following is an explanation of embodiments of the present invention. It should be noted that in the following embodiments, same components are referred to by the same reference numerals, and duplicate explanations are sometimes omitted.

Embodiment 1

FIG. 1 is a schematic drawing of one example of a plastic identifying apparatus of the present invention.

The example shown in FIG. 1 includes a sampling unit 2, which samples a test piece 1 from items 51 to be identified that contain plastic; an identifying unit 3, which is equipped with a detection unit 4 for identifying the types of plastics contained in the sampled test pieces 1; and a supply unit 5, which supplies the sampled test piece 1 from the sampling unit 2 to the detection unit 4.

Instead of directly identifying the items to be identified as in conventional methods, this plastic identifying apparatus samples a test piece and identifies the types of plastics contained in the sampled test piece. Therefore, it can carry out identification easily, even for large sized items to be identified, and the overall size of the apparatus can be very compact. Also, because such factors as the size and shape of the test piece can be optimized to suit the detection unit, accurate and consistent identification can be achieved regardless of the shape of the objects to be identified, and it is also suitable for continuous identification processes.

Note that, although FIG. 1 shows the back cover of a television receiver as the item 51 to be identified, there is no particular limitation to the shape, material, etc., of items to be identified as long as they contain plastic. Further, in the example shown in FIG. 1, the entire plastic identifying apparatus is positioned on a bench 52, however, the bench 52 is in no way a definite requirement. The plastic identifying apparatus of the present invention can be positioned at any location. Also, the respective relative positions of the sampling unit 2, the identifying unit 3, and the supply unit 5 can be freely arranged. As shown in the example of FIG. 1, when the sampling unit 2 and the identifying unit 3 are adjacent, the apparatus can be very compact, and the speed of the identification process can be enhanced.

There is no particular limitation on the identifying unit 3, as long as it is provided with a detection unit 4 that can identify the types of plastics contained in the test piece 1. For example, as shown in FIG. 1, it may be an arrangement with the detection unit 4 and a control unit 6 that controls the detection unit 4.

There is no particular limitation on the detection unit 4, as long as it can identify the plastic types contained in the test piece 1. For example, it may be a detection unit that utilizes methods using ordinary plastic analysis. These methods may be, for example, Raman spectrophotometry or infrared spectroscopy, etc.

The detection unit 4 may be a detection unit that uses a method in which infrared light of a predetermined wave number is irradiated onto the test piece 1 and the intensity of the infrared light that is totally reflected by the test piece 1 is detected (throughout this specification, this method is referred to as "infrared total reflection measurement method"). When using this method, even when the test pieces contain dark-colored plastics, or contain flame retardants, the types of plastics contained in the test pieces can be detected accurately. It should be noted that the above-mentioned predetermined infrared light wave number (also referred to below as "infrared light") is in the range, for example, of 400 $cm^{-1}$ to 4,000 $cm^{-1}$ (which puts this light into the category of ordinary mid infrared light).

When identifying the type of plastic contained in the test piece 1, infrared light can be irradiated on the test piece 1 while varying the wave number of the infrared light, and the intensity (or absorbance) of the totally reflected infrared light for each wave number can be detected. It is also possible to detect the intensity (or absorbance) of the totally reflected infrared light using Fourier transform infrared (FT-IR) spectroscopy. For example, wavelength-intensity distributions for predetermined plastics may be recorded in advance in a control unit 6, and by comparing them with the wavelength-intensity distribution obtained by the above-mentioned detection, the plastic types contained in the test piece 1 can be identified easily.

Figure 2:
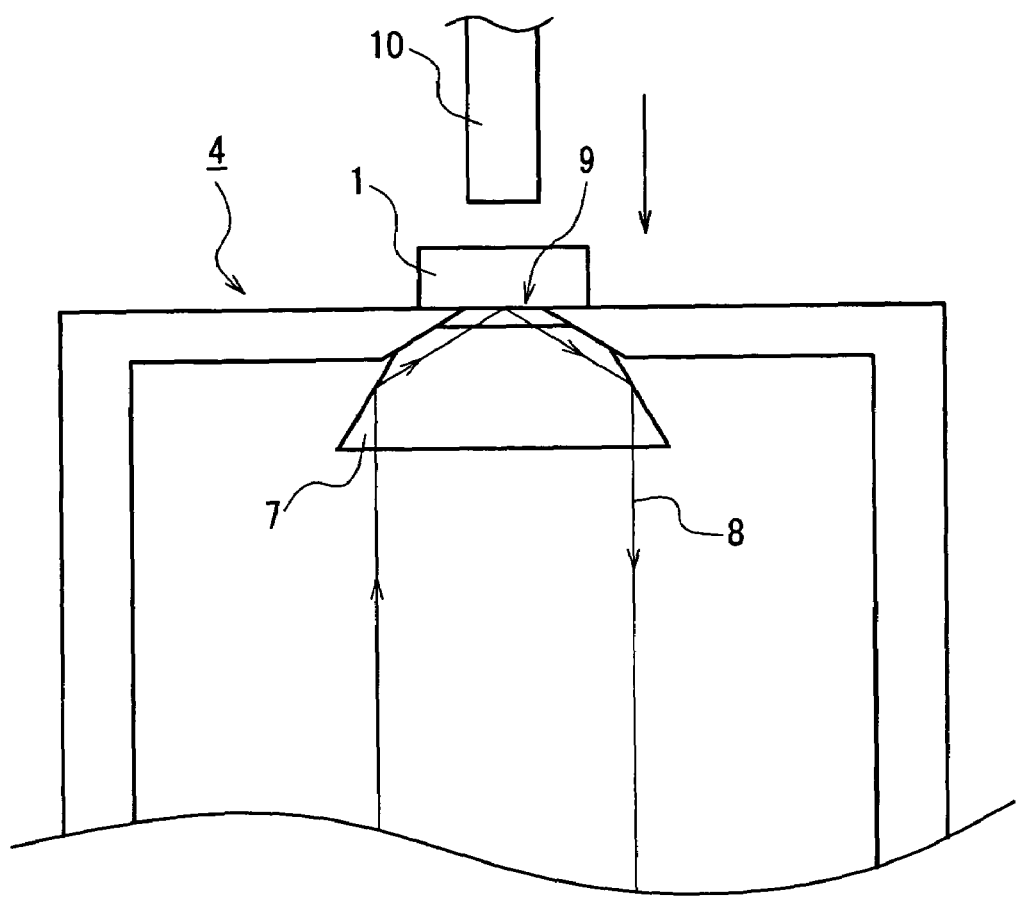
FIG. 2 is a cross-sectional view that shows an example of a detection unit in a plastic identifying apparatus of the present invention.

An example of a detection unit 4 that uses the above-mentioned infrared total reflectance measurement method is shown in FIG. 2. In the example shown in FIG. 2, the detection unit 4 is provided with a prism 7. The prism 7 irradiates infrared light 8 of a predetermined wave number from a detection aperture 9 onto the test piece 1. The incident infrared light 8 is totally reflected by the test piece 1, and after passing through the prism 7 again, its intensity is detected. Also, although not indicated, the detection unit 4 is provided with an infrared light source for outputting infrared light 8 and a detection device for measuring the intensity of the infrared light 8 that is totally reflected by the test piece 1. It should be noted that FIG. 2 is a cross-sectional view, but in order to make the drawing easier to view, hatching has been omitted. The same applies to other cross-sectional views hereinafter, except for FIG. 10.

In the plastic identifying apparatus of the present invention, it is also possible that the detection unit identifies at least two surfaces of the test pieces. For example, after the detection unit detects the wavelength intensity distribution for one surface of the test piece (for example, the surface corresponding to the front surface of the item to be identified), the test piece could be rotated so that the wavelength-intensity distribution of a surface different from the one just measured (for example, a surface that is first exposed during sampling) could be measured. Even when there is a coating on the surface of the item to be identified, or if the surface is degraded, because at least two surfaces of the test pieces sampled from the items to be identified are measured, the types of plastic contained in the test pieces can be identified more accurately. In order for the detection unit to measure at least two surfaces of the test pieces, the supply unit can be provided with, for example, a chucking unit, which will be explained later.

In the plastic identifying apparatus of the present invention, a pressing device can be provided to bring the test piece into contact with the detection unit. For example, as shown in FIG. 1, the identifying unit 3 can be provided with a pressing device 10. In the detection unit 4, as shown in FIG. 2, when identifying the plastic types contained in the test piece 1, if the pressing device 10 brings the test piece 1 into contact with the detection unit 4 (or in the example in FIG. 2, with the detection aperture 9 at which the infrared light is incident on the test piece 1), it becomes possible to identify the plastic types contained in the test piece 1 very reliably. It is very effective if, as shown in FIG. 2, the detection unit uses the infrared light total reflectance measurement method. As long as the test piece is brought into contact with the detection unit, there is no particular limitation to the structure, materials, or shape of the pressing device. For example, metals or glass could be used for the materials of the pressing device.

Figure 3:
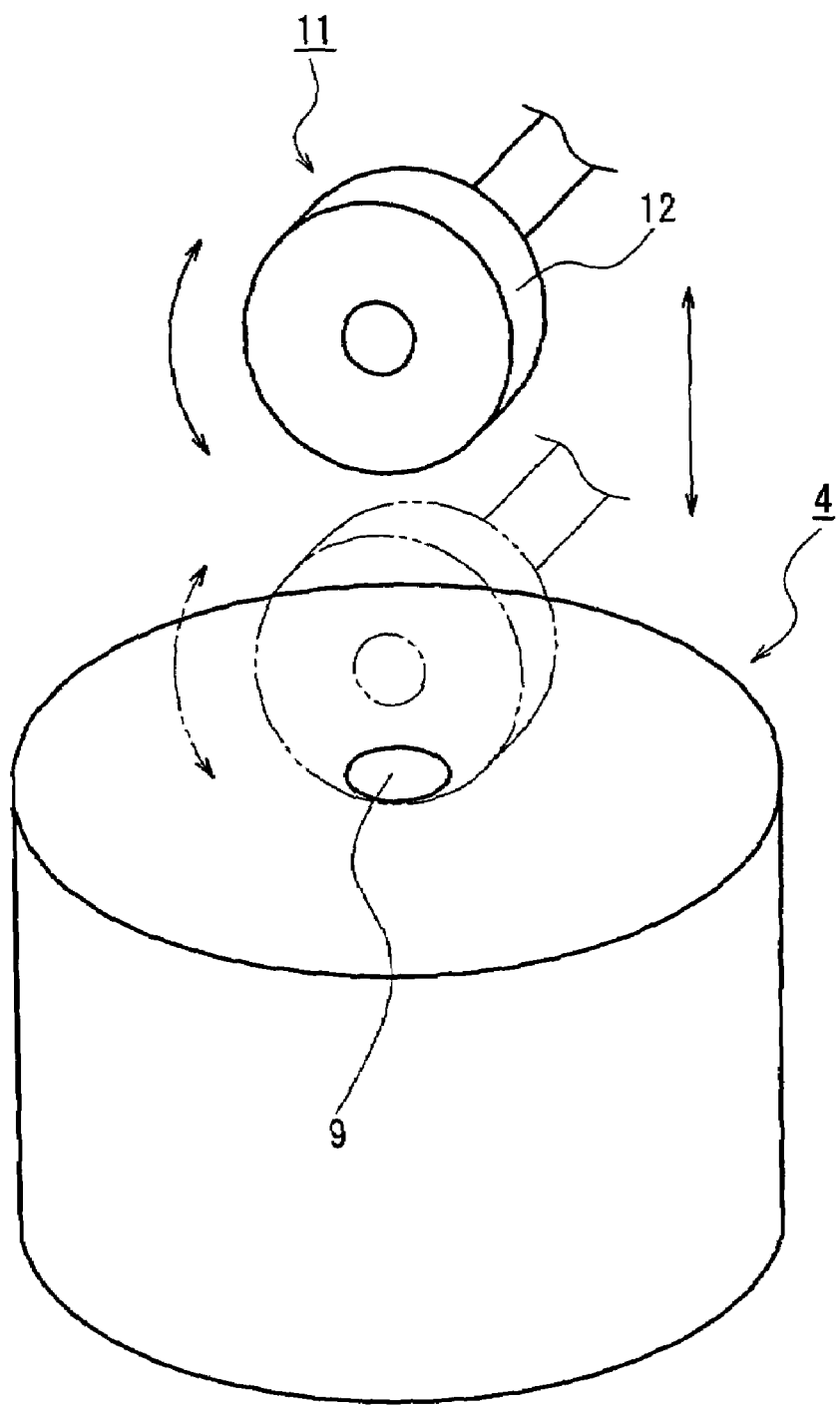
FIG. 3 is a schematic drawing showing an example of a cleaning unit cleaning a detection unit in a plastic identifying apparatus of the present invention.

In the plastic identifying apparatus of the present invention, the detection unit may be provided further with a cleaning unit. FIG. 3 shows an example of this.

The cleaning unit 11 shown in FIG. 3 is provided with a rotatable brush 12. When cleaning the detection unit 4, the brush 12 can be rotated after being brought into contact with the detection unit 4. The area in which cleaning is performed in the detection unit 4 can be freely adjusted, as required. For example, as shown in FIG. 3, if the brush 12 is rotated after being brought into contact with the detection aperture 9, it is possible to clean the vicinity of the detection aperture 9 in the detection unit 4. Further, when not performing cleaning, the cleaning unit 11 can be made to stand by at a predetermined position so as not to interfere with the identification of test pieces. It is also possible to provide the identification unit 3 with a cleaning unit 11.

The timing for the cleaning of the detection unit 4 by the cleaning unit 11 can be before or after, or before and after the measurement of the test piece. Further, the cleaning method is not limited to the method of rotating a brush as shown in FIG. 3. For example, it is also possible to clean the detection unit by sliding a brush left and right. Also, instead of a brush, cleaning can also be performed by blowing air onto the detection unit. As long as the detection unit 4 can be cleaned, there is no particular limitation to the structure, materials, or shape of the cleaning unit. For example, a cloth or sponge could be used as the material for the brush 12 of the cleaning unit 11 shown in FIG. 3.

Identification of the test pieces can be affected adversely by dust adhering to the detection unit, or by debris or the like adhering to the test pieces. When a cleaning unit for cleaning the detection unit is further provided, it can remove the dirt, etc., that adheres to the detection unit. And for this reason, the types of plastics contained in the test pieces can be identified with greater accuracy and consistency.

As for the sampling unit of the plastic identifying apparatus of the present invention, as long as it can sample test pieces from the items to be identified, there is no particular limitation to its structure, etc. For example, it may be provided with a means for punching test pieces from the items to be identified. There are various conceivable methods for sampling test pieces from the items to be identified, such as cutting, etc., but using a punching method allows test pieces to be sampled very easily.

As for the above-mentioned punching means, a punch press, for example, or similar may be used. In the example shown in FIG. 1, the sampling unit 2 is fitted with a punch press 13.

As for the supply unit in the plastic identifying apparatus of the present invention, as long as it can supply test pieces from the sampling unit to the detection unit, there is no particular limitation to its structure etc. For example, as shown in FIG. 1, the supply unit 5 may be provided with a chucking unit 14 to hold the test piece 1 that has been sampled by the sampling unit 2. If the test piece 1 is supplied to the detection unit 4 by the chucking unit 14, the type of plastic contained in the test piece 1 can be identified with accuracy and consistency.

When the supply unit is provided with a chucking unit, the chucking unit can hold the test piece at the sampling unit and supply it as is to the detection unit. Furthermore, as shown in the example in FIG. 1, the supply unit 5 can be provided with a test piece transport unit 15 (for transporting the test piece 1 from the sampling unit 2 to the chucking unit 14) and the chucking unit 14.

In the example shown in FIG. 1, the test piece 1 punched by the punch press 13 drops as it is and is then stored by a test piece holder that is positioned inside the test piece transport unit 15. The test piece holder that stores the test piece 1 moves along a guide rail inside the test piece transport unit 15, and approaches the vicinity of the chucking unit 14, thus transporting the test piece 1 to the chucking unit 14. At that stage, if the chucking unit 14 is not holding anything, the test piece 1 can be supplied as is to the detection unit 4 by the chucking unit 14. If the chucking unit 14 is holding another test piece, the test piece 1 being transported by the test piece transport unit 15 can be made to stand by where it is, then supplied to the detection unit 4 after waiting for the chucking unit 14 to become free.

In this case, while one test piece is being identified at the detection unit 4, another test piece can be sampled and transported to the vicinity of the chucking unit 14 by the test piece transport unit 15. For this reason, the steps of sampling and transporting the test pieces can be performed in parallel to the steps of supplying the transported test pieces to the detection unit and identifying them, thus affording improved identification capabilities. And for this reason, it becomes easy to implement continuous identification operations.

There is no particular limitation to the structure, etc., of the test piece transport unit 15, as long as it can transport the test pieces 1 from the sampling unit 2 to the chucking unit 14. For example, it could be configured as a test piece transport unit using such items as belts, slide rails, or air-driven components.

Furthermore, the chucking unit may be provided with a rotation unit that rotates test pieces around a horizontal rotational axis. In this case, at least two surfaces of the test pieces can be identified very easily. An example of such a chucking unit is shown in FIGS. 4A and 4B.

Figure 4A:
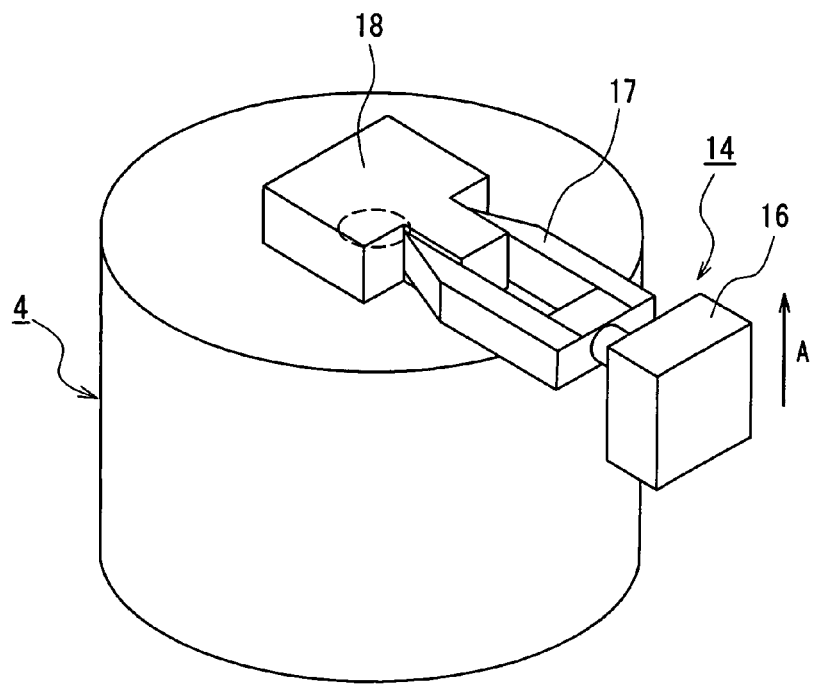
FIGS. 4A and 4B are schematic drawings showing an operational example of a chucking unit in a plastic identifying apparatus of the present invention.
Figure 4B:
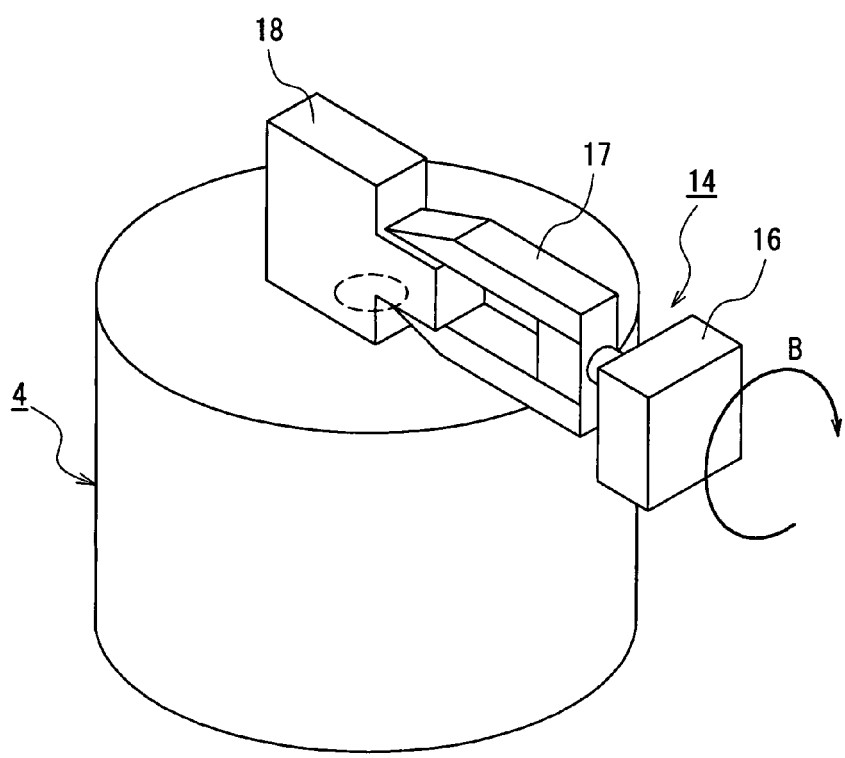

In the examples shown in FIGS. 4A and 4B, the chucking unit 14 is equipped with a rotation unit 16 and a chuck 17. While a test piece 18 is held by the chuck 17 with the rotation unit 16, rotation around a horizontal rotational axis (a horizontal direction perpendicular to the direction of axis A in FIG. 4A) is achieved (that is, the test piece 18 can rotate around a horizontal axis). As long as the rotation unit 16 can rotate the test piece 18, which is held by the chuck 17, in the above-mentioned manner, there is no particular limitation to its structure, etc. Further, as long as the chuck 17 can hold the test piece 18, there is no particular limitation to its structure, etc.

The chuck 17 shown in FIGS. 4A and 4B can be moved vertically (direction of axis A in FIG. 4A) in order to position the test piece 18 on the detection unit 4. It is also possible to move the entire chucking unit 14 up and down by moving the rotation unit 16 up and down. In this case, as long as the rotation unit 16 can rotate the test piece 18 held by the chuck 17 in the above-mentioned manner, and as long as the rotation unit 16 itself can move up and down, there is no particular limitation to its structure.

FIGS. 4A and 4B will be used to explain the process by which identification is performed for at least two surfaces of the test piece 18.

First, as shown in FIG. 4A, the test piece 18, which was sampled by the sampling unit, is held by the chuck 17 and positioned above the detection unit 4. The test piece 18 is in the approximate shape of a "T," and test pieces such as this can be obtained, for example, by using a die provided with a "T" shape to punch press the items to be identified.

After the test piece 18 is positioned, the identification for the type of plastic contained in one of its surfaces is performed by the detection unit 4. At this time, the test piece 18 can be brought into contact with the detection unit 4 by the above-mentioned pressing device. The operation of the chuck 17 when a pressing device is used will be discussed later.

After this identification, the chuck 17, which is holding the test piece 18, is raised once in the A-axis direction shown in FIG. 4A. Then, as shown in FIG. 4B, the chuck 17 (that is, the test piece 18), is rotated by the rotation unit 16 at least 90° in the direction indicated by arrow B. After this rotation, the chuck 17 is lowered again in the A-axis direction, and a surface of the test piece 18 that is different from the previous surface is positioned above the detection unit 4, so that this different surface can be identified for the type of plastic contained therein. In this way, identification for at least two surfaces of the test piece 18 can be performed very easily. Note that the angle of rotation for the test piece is not limited to the above-mentioned 90°, but can be freely adjusted to suit the shape of the test piece.

Figure 5:
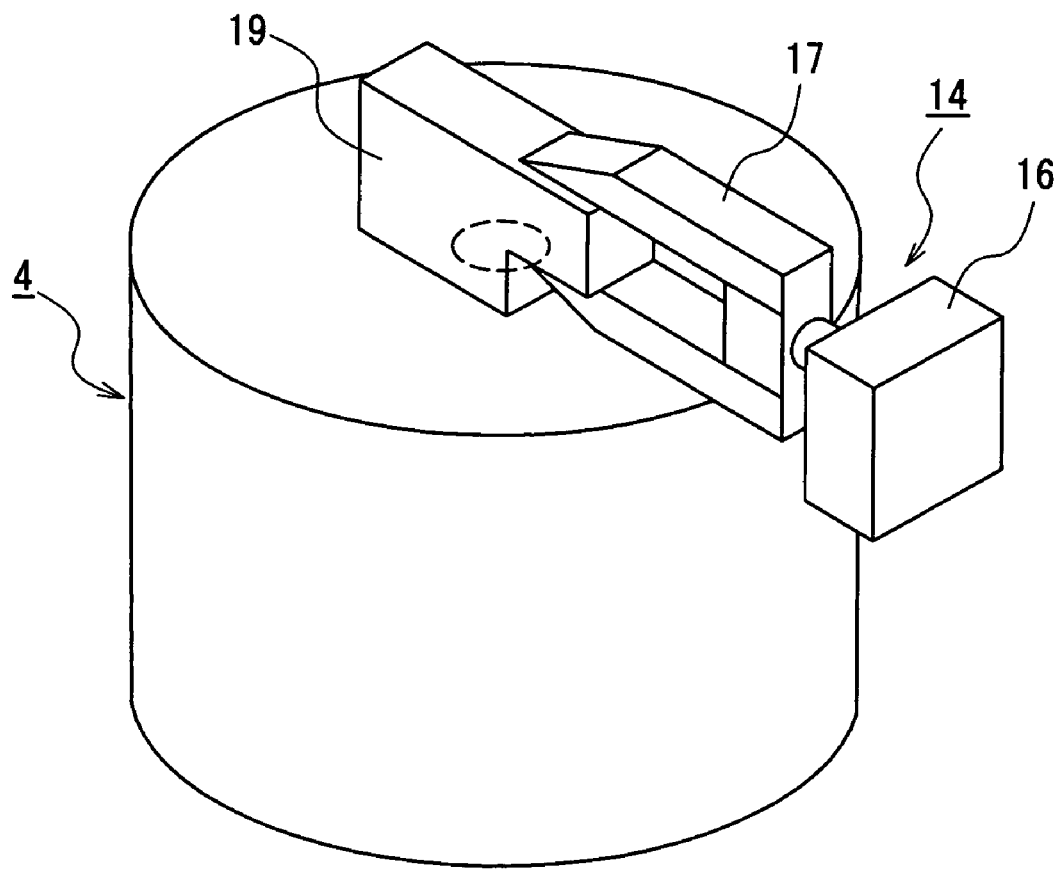
FIG. 5 is a schematic drawing showing an examplary shape of a test piece in the present invention.

There is no particular limitation to the shape of the test pieces. For example, the shape can be that of the "T" shaped test piece 18 shown in FIGS. 4A and 4B, or the "L" shaped test piece 19 shown in FIG. 5. In these circumstances, because there is no interference between the chuck 17 and the upper surface of the detection unit 4 for the series of steps described above of identifying at least two of the surfaces of the test piece, this series of steps can be performed very smoothly.

Figure 6:
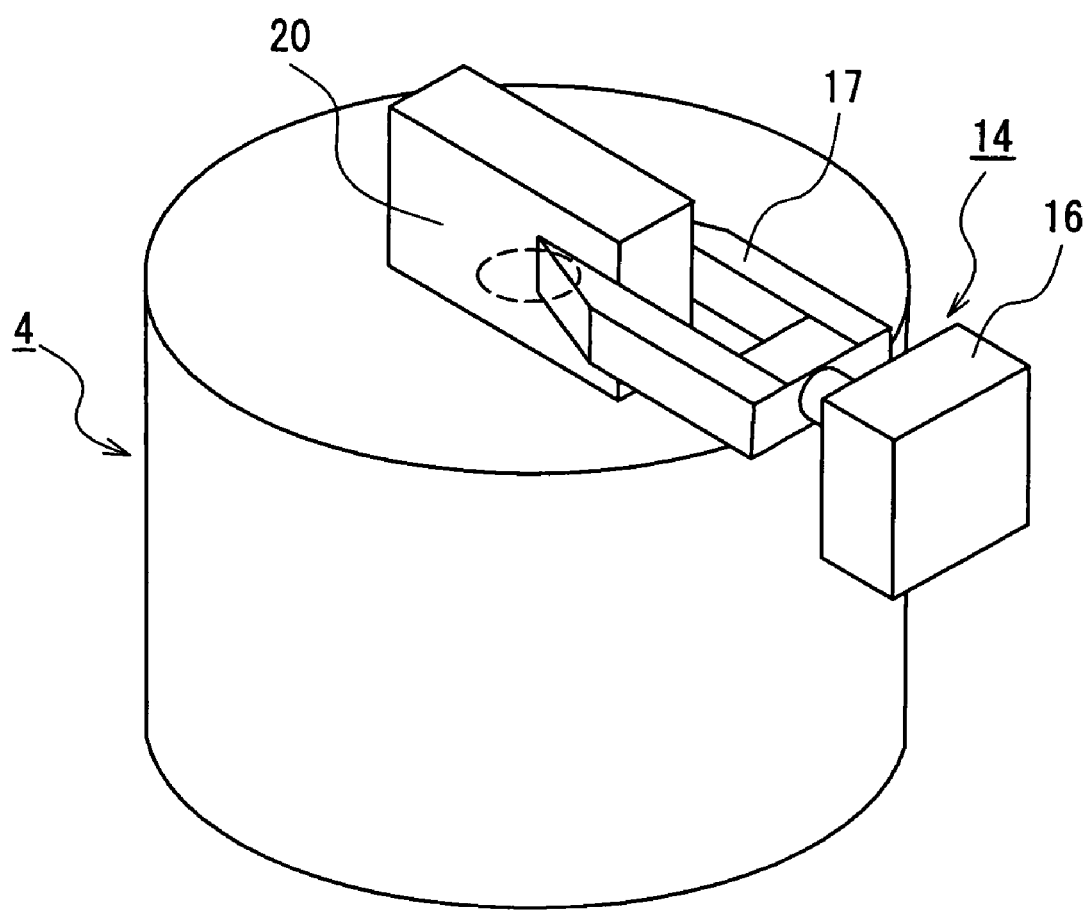
FIG. 6 is a schematic drawing showing another examplary shape of a test piece in the present invention.
Figure 7:
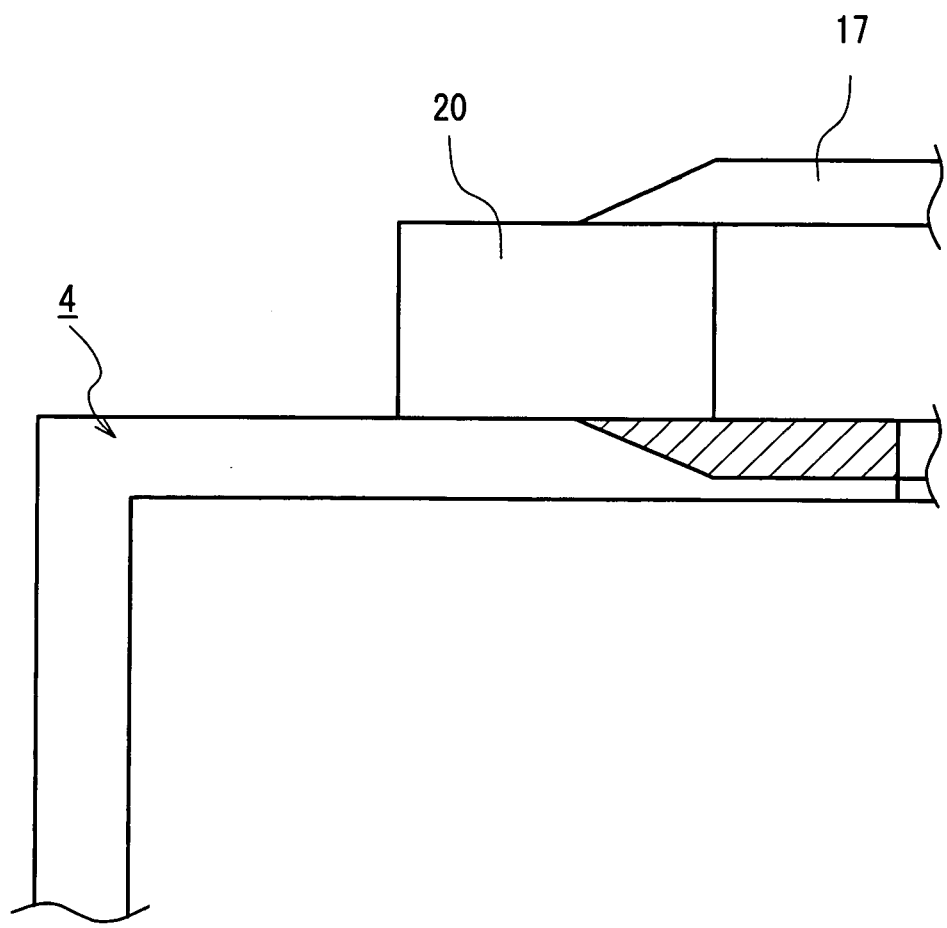
FIG. 7 is a cross-sectional view that shows an example of the relationship between a test piece and a detection unit.

For example, when the test piece 20 has an approximate rectangular shape as shown in FIG. 6, there is the possibility of interference occurring between the chuck 17 and the upper surface of the detection unit 4 during the above-mentioned series of steps. For example, after the detection unit 4 has identified one surface of the test piece 20, the chuck 17, which is holding the test piece 20, is raised once and then the chuck 17 (that is, the test piece 20) is rotated at least 90°, then, after this rotation, when attempting to position the test piece 20 again over the detection unit 4, if left in this manner there will be interference between the chuck 17 and the upper surface of the detection unit 4 as shown in FIG. 7 (the shaded area in FIG. 7 is the area of interference). This interference can be resolved by either rotating the test piece by 180°, or by horizontally changing the grip of the chuck 17 on the test piece when repositioning the test piece 20 after rotation, thereby allowing measurement of the test piece 20 without problem. However, when the test piece is in either an approximate "T" shape or an approximate "L" shape, the test piece can be repositioned without any change of grip on the test piece. For this reason, it is possible to eliminate chucking errors that could cause the test piece to come loose and fall, or the like, and identification for the plastic types contained in the test piece can be performed with greater consistency.

Figure 8:
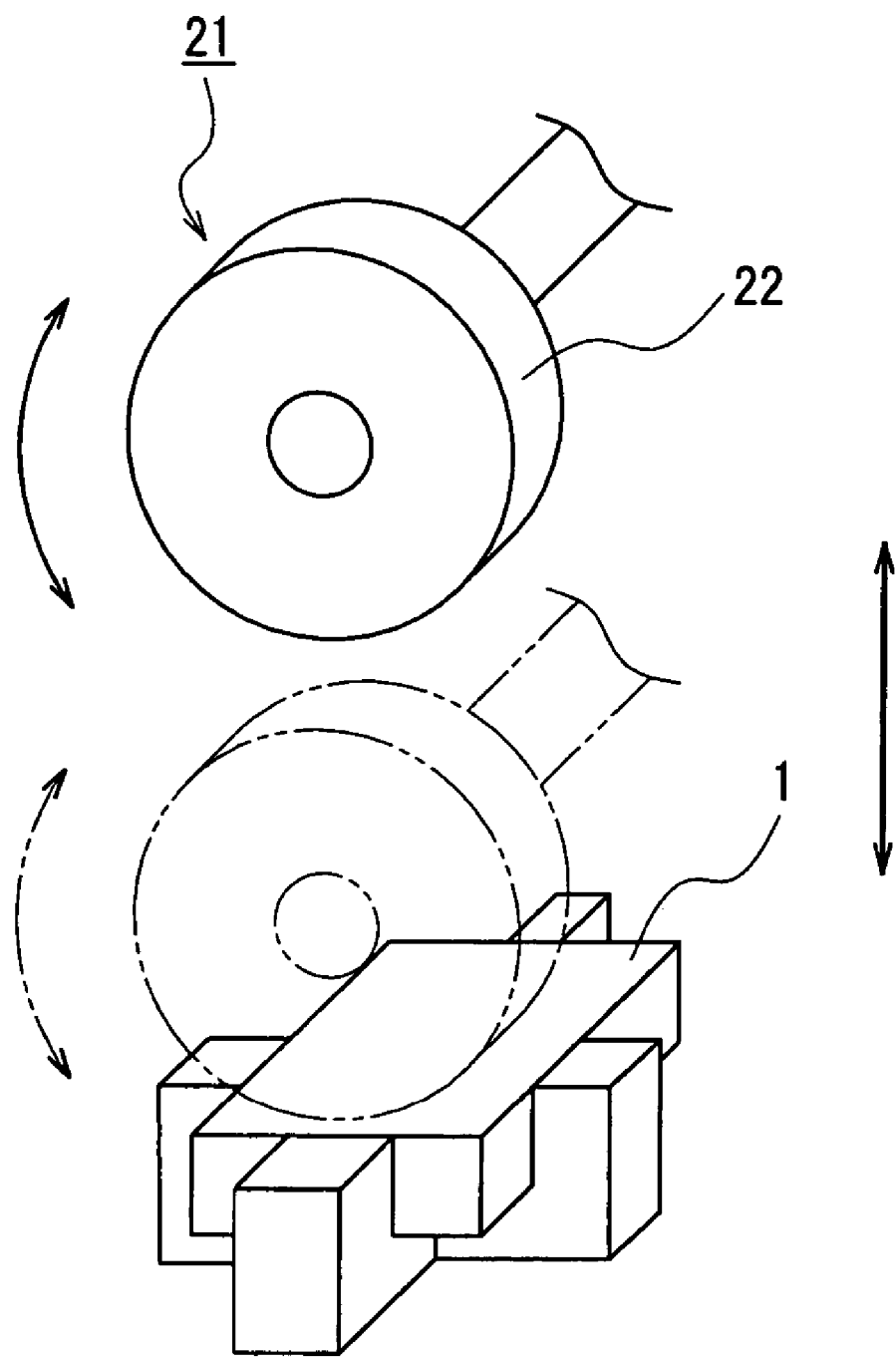
FIG. 8 is a schematic drawing showing an example of a cleaning unit cleaning the surface of a test piece in a plastic identifying apparatus of the present invention.

The plastic identifying apparatus of the present invention can be provided further with a cleaning unit for cleaning the surfaces of the test pieces. FIG. 8 shows an example of this.

In the example shown in FIG. 8, a cleaning unit 21 is provided with a rotatable brush 22. To clean the surface of the test piece 1, the brush 22 is lowered until it contacts the test piece 1, and after contact has been made, the brush 22 can be rotated. Note that, as long as it can perform surface cleaning for the test piece 1, there is no particular limitation to the structure, materials, or form of the cleaning unit 21. For example, the material used for the brush 22 shown in FIG. 8 may be cloth, sponge, or similar.

The cleaning unit 21 can be positioned in any desired location, from the sampling unit 2 shown in FIG. 1 to the detection unit 4. For example, it can be positioned at the test piece transport unit 15. In this case, the surface of the test piece 1 can be cleaned before the test piece 1 sampled by the sampling unit 2 is transported to the chucking unit 14. Also, this cleaning can be performed by temporarily stopping the transport of the test piece 1 and bringing the brush 22 into contact with the stopped test piece 1 as shown in FIG. 8. Also, the position of the brush 22 can be determined in advance and cleaning can be performed by bringing the brush 22 into contact during the transport of the test piece 1. Note that, in addition to performing cleaning by brush rotation as shown in FIG. 8, cleaning can be performed by having the brush slide left and right.

Foreign matter, such as dirt that adheres to the surface of the test pieces, can be removed by providing a cleaning unit such as this, thus allowing types of plastics contained in the test pieces to be identified with greater accuracy and consistency.

The plastic identifying apparatus of the present invention can be provided further with a pressing unit to press the surface of the test pieces. An example of this is shown in FIG. 9.

Figure 9:
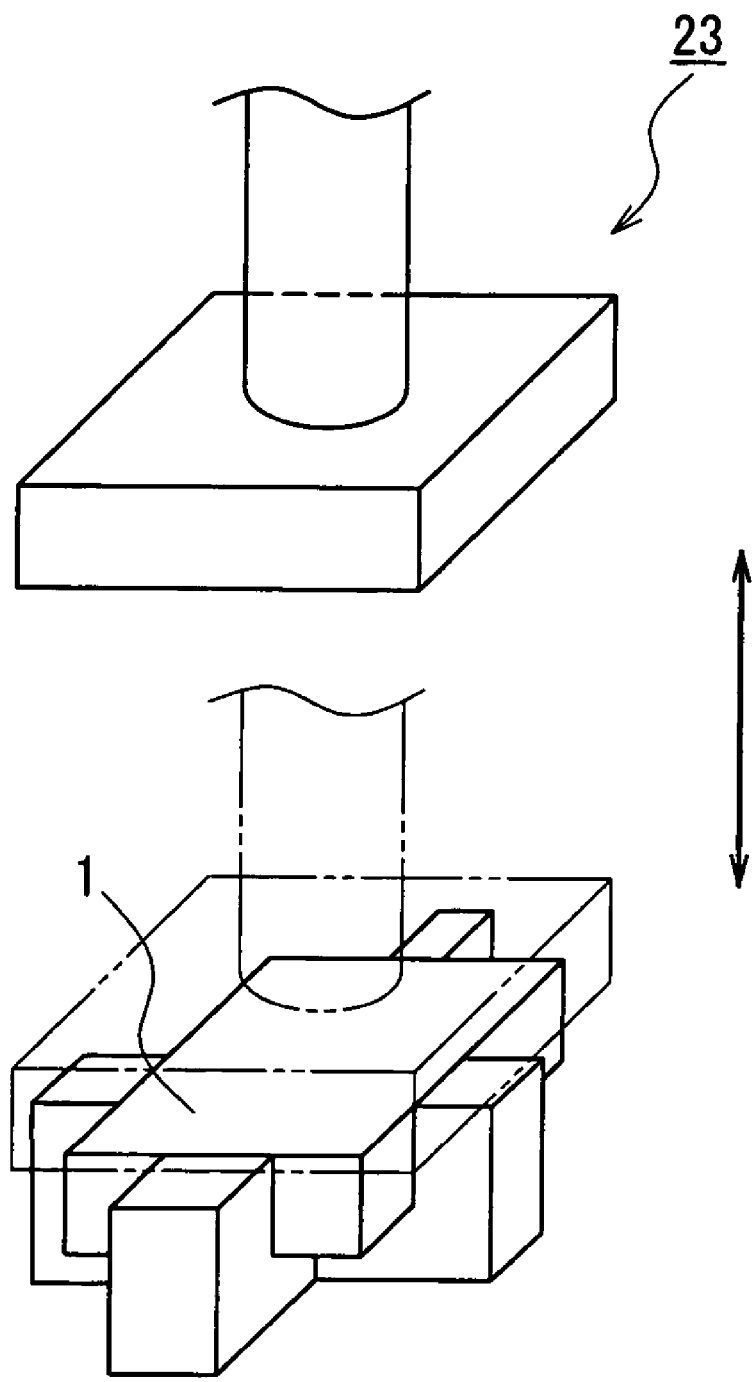
FIG. 9 is a schematic drawing showing an example of a pressing unit pressing against the surface of a test piece in a plastic identifying apparatus of the present invention.

By pressing the surface of the test piece 1 with a pressing unit 23 as shown in FIG. 9, the surfaces of test piece 1 can be provided with uniformity. As long as it can provide uniformity for the surfaces of test piece 1, there is no particular limitation to the structure, materials or form of the pressing unit 23. For example, metals, glass, or the like may be used for the surface of the pressing unit 23 that contacts the test piece 1.

The pressing unit 23 can be positioned in any desired location from the sampling unit 2 shown in FIG. 1 to the detection unit 4. For example, it can be positioned at the test piece transport unit 15. In this case, the surfaces of the test pieces 1 can be pressed and provided with uniformity before the test piece 1 sampled by the sampling unit 2 is transported to the chucking unit 14.

Figure 10:
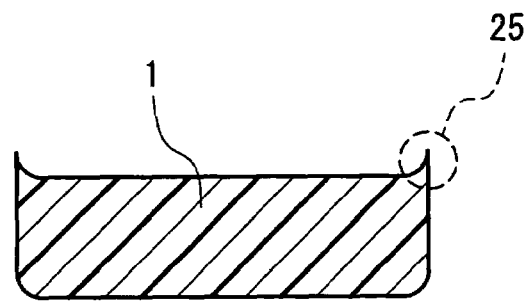
FIG. 10 is a cross-sectional view of an example of a test piece that has burrs.
Figure 11:
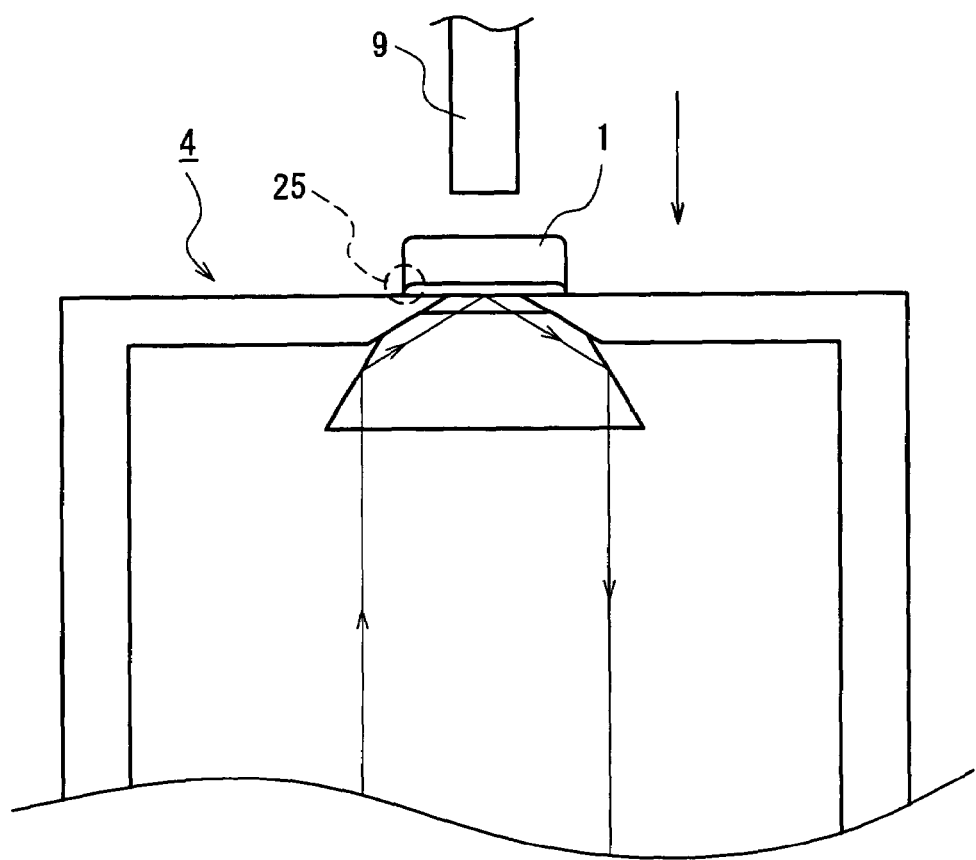
FIG. 11 is a cross-sectional view that shows an example of the relationship between a test piece and a detection unit.

The following is an explanation of "surface uniformity." As shown in FIG. 10, depending on the sampling method, there may be a burr 25 on the edges of test piece 1 sampled by the sampling unit. When burrs such as these are present on the test pieces, it is possible that, as shown in FIG. 11, when the test piece is to be positioned over the detection unit for identification, it is not possible to bring the test piece 1 into contact with the detection unit 4 due to the burr 25. This is also the same even when a pressing device 9 presses the test piece 1 to the detection unit 4. When the test piece 1 cannot be brought into contact with the detection unit 4, there is the possibility that the accuracy of identifying the plastic types contained in the test pieces 1 will be affected adversely. For this reason, it is preferable that the presence of protruding portions such as burrs on the test pieces is minimized, and that the surfaces are as uniform as possible.

When the plastic identifying apparatus is provided with a pressing unit 23 as shown in FIG. 9, greater accuracy and consistency can be achieved in the identification of the plastic types contained in the test pieces, because the presence of burrs on the test pieces can be minimized. Note that in the example of the detection unit 4 shown in FIG. 11, although the detection unit there uses the infrared total reflectance measurement method shown in FIG. 2, the same applies even if the method used is a different method.

Further, the plastic identifying apparatus of the present invention also can be provided with polishing unit to provide uniformity for the surfaces of the test pieces. Similar to the above-mentioned situation in which a pressing unit is provided, the identification of the plastic types contained in the test pieces can be performed with greater accuracy and consistency, because the presence of burrs on the test pieces can be minimized.

Furthermore, after identifying the plastic types contained in test pieces using the plastic identifying apparatus of the present invention, the items to be identified, which have had test pieces sampled, can be sorted based on those results. For that purpose, for example, in addition to the plastic identifying method of the present invention, object sorting apparatuses, or a control system that links plastic identifying apparatuses with object sorting apparatuses can be provided. In this case, the following procedure, for example, can be performed.

First, test pieces are sampled from the items to be identified by the plastic identifying apparatus. Next, the plastic types contained in the test pieces (that is, the plastic types contained in the items to be identified) are identified by the plastic identifying apparatus. Meanwhile, items to be identified are transported to an object sorting apparatus. The results of the above-described identification process are transmitted to the object sorting apparatus via a control system, and the items are sorted based on these results. Note that, as long as the object sorting apparatus can sort identified objects, there is no particular limitation to its structure, etc.

Embodiment 2

One example of an embodiment of the plastic identifying method of the present invention will be explained using the example of a plastic identifying apparatus shown in FIG. 1.

The plastic identifying method of the present invention includes, (i) a step of sampling the test piece 1 from the item 51 to be identified that contains plastic, (ii) a step of supplying the sampled test piece 1 to a detection unit 4 for identification of the plastic types contained in the test pieces, and (iii) a step of identifying the plastic types contained in the test piece 1 with the detection unit 4.

Instead of directly identifying the items to be identified as in conventional methods, in this plastic identifying method, test pieces are sampled and these test pieces then are identified. Therefore, identification can be performed easily, even for large objects to be identified, and the overall equipment size can be made very compact. Also, because such factors as the size and shape of the test pieces can be optimized to suit the detection unit regardless of the shape of the objects to be identified, very accurate and stable identification can be performed, and it is possible to anticipate continuous identification processes.

For sampling the test pieces 1 from the items 51 to be identified that contain plastics, as shown in FIG. 1, the items 51 to be identified can be set in the sampling unit 2 and the test pieces 1 can be punched out by the punch press 13. Also, when supplying the sampled test pieces 1 to the detection unit 4, the test pieces 1 are first transported by the test piece transport unit 15 from the sampling unit 2 to the chucking unit 14, then the transported test pieces 1 can be supplied to the detection unit 4 by the chucking unit 14. Note that this series of steps can be automated.

In the plastic identifying method of the present invention, for identification by the detection unit of the plastic types contained in the test piece, infrared light of a predetermined wave number can be irradiated onto the item to be identified, and the intensity of the infrared light that is totally reflected by this item can be detected. When using this method (infrared total reflectance measurement method), the type of plastic contained in the test piece can be identified very accurately, even in cases when the test piece includes dark-colored plastic, or in cases when the test piece contains flame retardants. Note that the above-mentioned predetermined infrared light wave number is in a range, for example, from 400 $cm^{-1}$ to 4,000 $cm^{-1}$. In order to implement this method, it is possible to use, for example, the example detection unit shown in FIG. 2, which uses an infrared total reflectance measurement method.

In the plastic identifying method of the present invention, when the detection unit is identifying the plastic types contained in the test piece, the test piece can be brought into contact with the detection unit. If the test piece is brought into contact with the detection unit, the type of plastic contained in the test piece can be identified with greater certainty. In particular, a detection unit using the above-mentioned infrared total reflectance measurement method is particularly effective. In order to bring the test piece into contact with the detection unit, it is possible to use, as shown in FIG. 1 for example, a pressing device 10.

Figure 12:
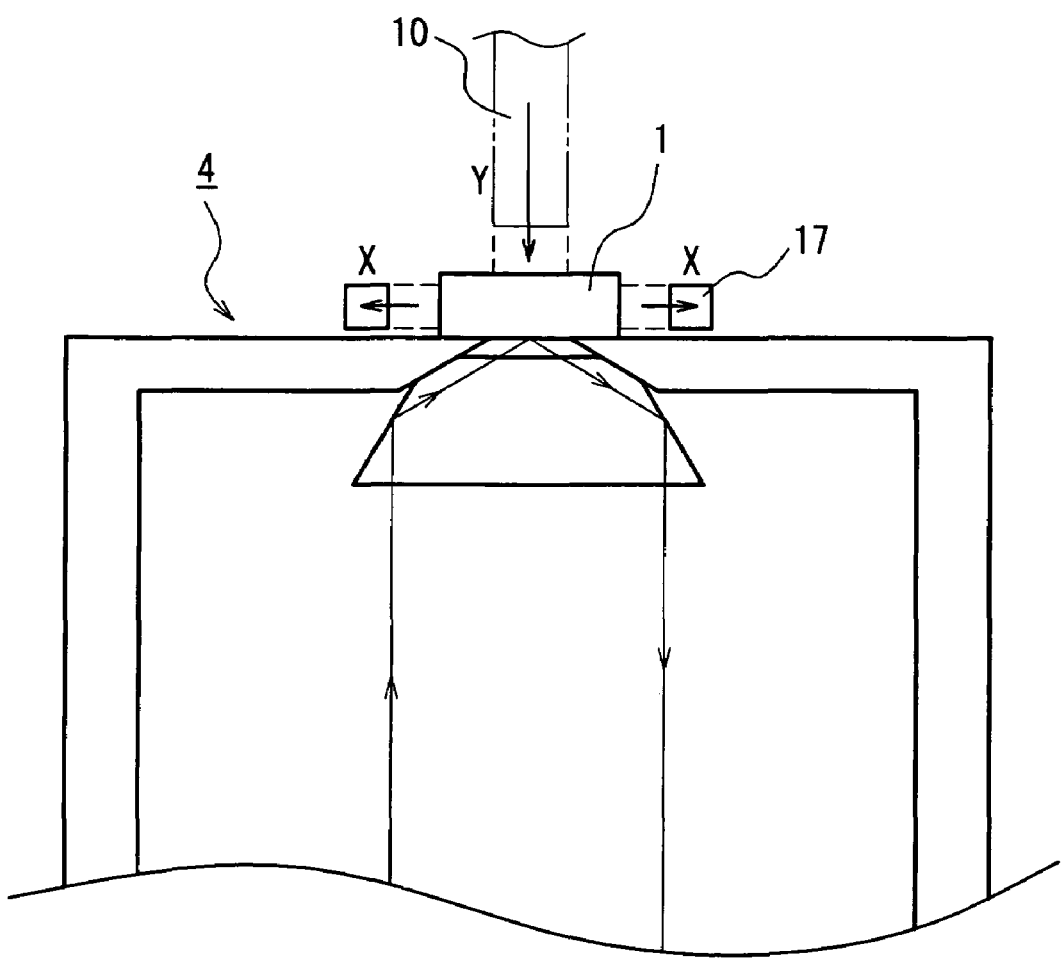
FIG. 12 is a cross-sectional view that shows an operational example of a chucking unit in the present invention.

Furthermore, when bringing a test piece into contact with the detection unit, the test piece can be brought into contact with the detection unit after letting the test piece become stationary above the detection unit. For example, when using the pressing device 10 shown in FIG. 1 as a method for bringing these into contact, it is possible to use a chucking unit 14, the operation of which is explained in an example below (explained using FIG. 12). Note that the chucking unit is provided with a chuck that holds the test piece, but in order to simplify the explanation, only the chuck is shown in FIG. 12. Also, "stationary" as used in this specification refers to a placement state that is independent of and not supported by any means. No consideration is given to the duration of this state.

As shown in FIG. 12, the test piece 1 is first positioned over the detection unit 4 by a chuck 17, after which the chuck 17 is opened (moved in the directions indicated by the X arrows in FIG. 12) and the test piece 1 is released and allowed to become stationary. Next, the pressing device 10 is moved in the direction indicated by the Y arrow in FIG. 12, and the test piece 1 is brought into contact with the detection unit 4. While kept in contact in this manner, identification is performed for the plastic types contained in the test piece 1. After this identification is finished, the pressing device 10 is separated from the test piece 1 and then the test piece 1 is again held by the chuck 17, so that the test piece 1 can be transported from the detection unit 4.

Figure 13:
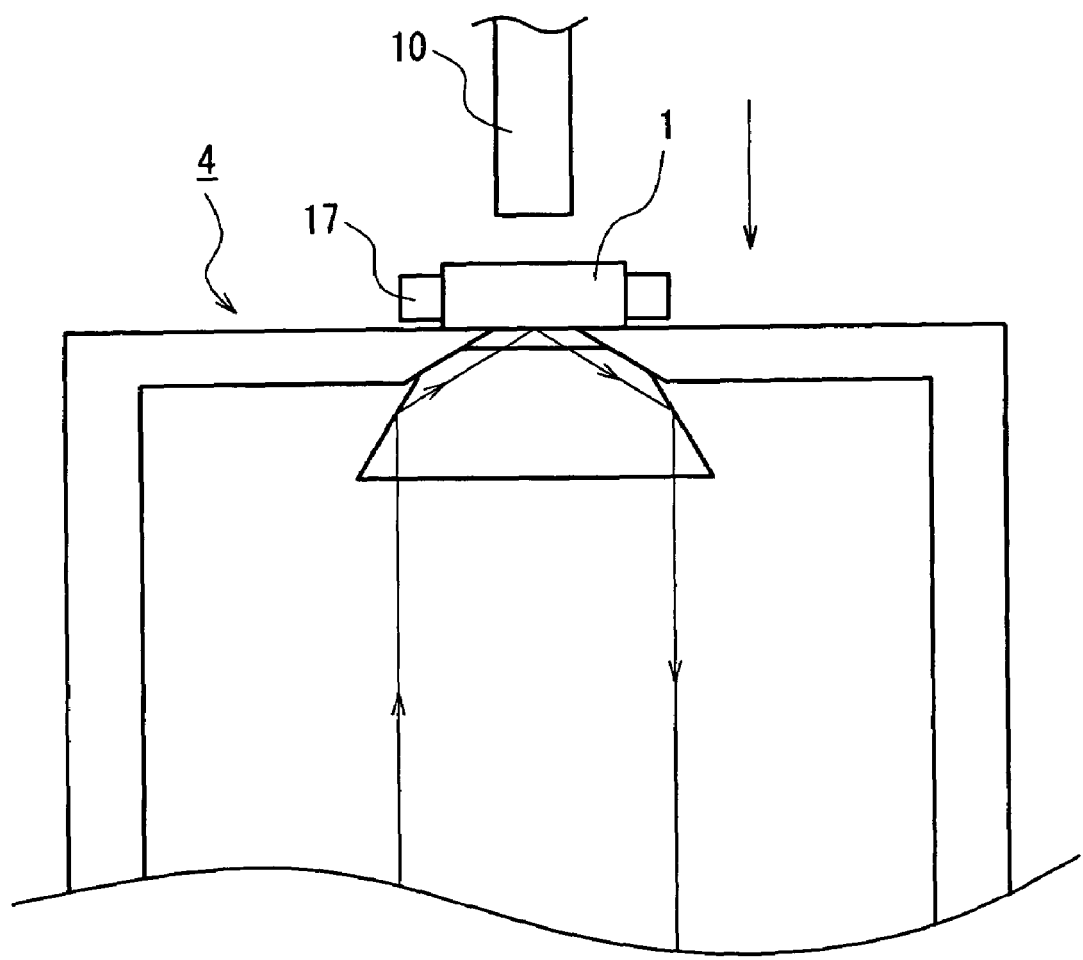
FIG. 13 is a cross-sectional view that shows an example of the relationship between a test piece and a detection unit.
Figure 14:
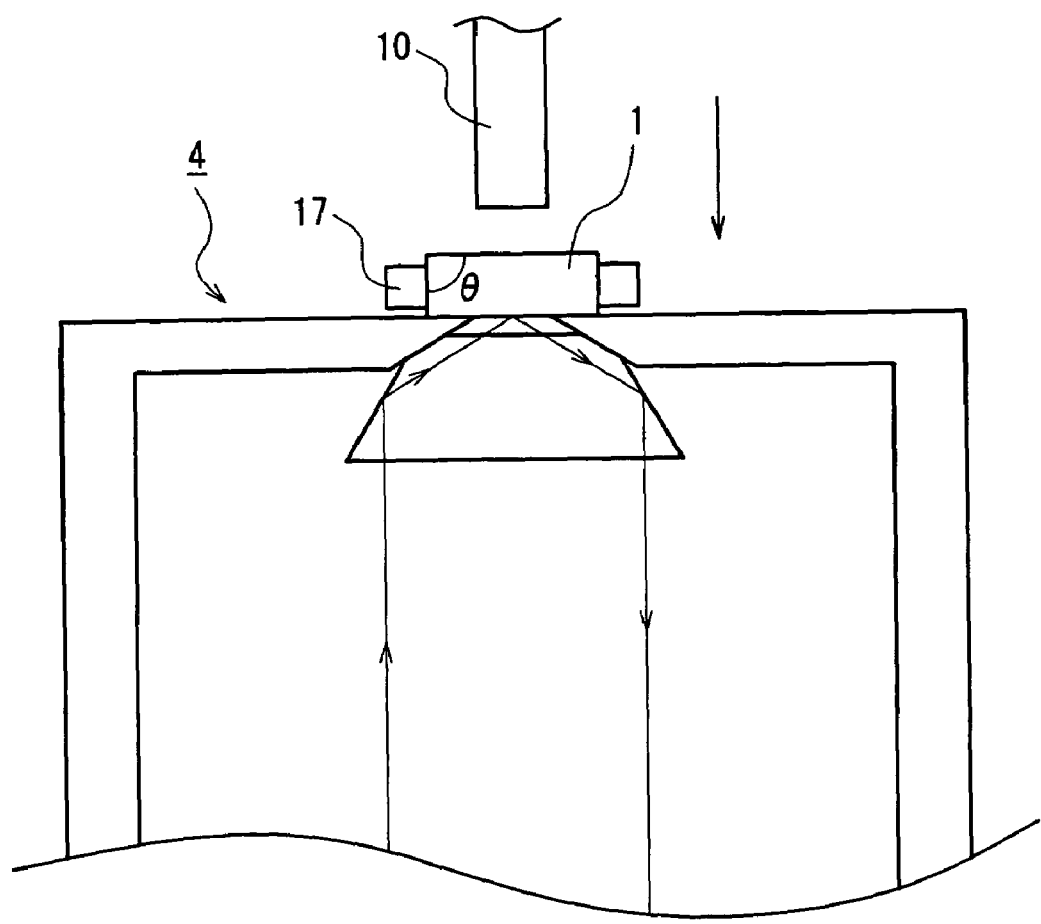
FIG. 14 is a cross-sectional view that shows an example of the relationship between a test piece and a detection unit.

At this time, as shown in FIG. 13, if the pressing device 10 presses while the test piece 1 is being held by the chuck 17, there is the possibility that the test piece 1 will be pushed upon the detection unit 4 in an orientation tilted against the chuck 17. Furthermore, as shown in FIG. 14, when the angle θ between the upper and side surfaces of the test piece 1 is not a right angle, it is possible that the test piece 1 could be brought into contact with the detection unit 4 with an uneven force, or the detection unit 4 and the test piece 1 might not be brought into contact, or similar.

Even in these kinds of situations it is possible to identify the plastic types contained in the test piece 1. However, as stated above, when the chuck opens and releases the test piece and the test piece becomes stationary before it is pressed by the pressing device, the test piece and the detection unit can be better brought into contact. Therefore, identification of the plastic types contained in the test pieces can be performed with greater accuracy and consistency. Note that although the detection unit 4 shown in FIGS. 12 to 14 is the detection unit shown in FIG. 2 that uses an infrared total reflectance measurement method, the same applies for detection units that use other methods.

In the plastic identifying method of the present invention, it is also possible to perform identification for at least two sides of the test piece. Even in situations such as when surface coatings have been applied, or when there is surface degradation due to long use, the plastic types contained in the test pieces can be identified with greater certainty when at least two surfaces of the test pieces sampled from the items to be identified are measured.

The present invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description. All changes that come within the meaning and range of equivalency of the claims are intended to be embraced therein.

INDUSTRIAL APPLICABILITY

With the plastic identifying apparatus or plastic identifying method of the present invention, the plastics contained in items to be identified can be identified with good accuracy, and continuously, regardless of the size of the items to be identified.

The invention claimed is:

1. A plastic identifying apparatus comprising:
a sampling unit that samples a test piece from an item to be identified that contains plastic;
an identifying unit provided with a detection unit that identifies a type of plastic contained in the test piece; and
a supply unit that supplies the test piece from the sampling unit to the detection unit,
wherein the supply unit comprises a chucking unit that rotates the test piece sampled by the sampling unit while holding the test piece so that at least two surfaces of the test piece are positioned at the detection unit.

2. The plastic identifying apparatus according to claim 1, wherein the detection unit irradiates infrared light of a predetermined wave number onto the test piece, and detects the intensity of the infrared light that is totally reflected by the test piece.

3. The plastic identifying apparatus according to claim 1, further comprising a pressing device that brings the test piece into contact with the detection unit.

4. The plastic identifying apparatus according to claim 1, further comprising a cleaning unit that cleans the detection unit.

5. The plastic identifying apparatus according to claim 1, wherein the sampling unit comprises a means for punching a test piece from the item to be identified.

6. The plastic identifying apparatus according to claim 5, wherein the punching means is a punch press.

7. The plastic identifying apparatus according to claim 1, wherein the chucking unit comprises a rotation unit that rotates the test piece around a horizontal rotational axis while the chucking unit holds the test piece.

8. The plastic identifying apparatus according to claim 1, wherein the shape of the test piece is an approximate "T" shape or an approximate "L" shape.

9. The plastic identifying apparatus according to claim 1, wherein the chucking unit comprises a rotation unit that arranges at least two sides of the test piece at the detection unit.

10. The plastic identifying apparatus according to claim 1, further comprising a cleaning unit that cleans a surface of the rest piece.

11. The plastic identifying apparatus according to claim 1, further comprising a pressing unit that presses against a surface of the test piece.

12. The plastic identifying apparatus according to claim 1, further comprising a polishing unit that provides a surface of the test piece with uniformity.

13. A plastic identifying method comprising:
(i) a step of sampling a test piece from an item to be identified that contains plastic,
(ii) a step of supplying the sampled test piece to a detection unit for identification of a type of plastic contained in the test piece, and
(iii) a step of identifying the type of plastic contained in the test piece with the detection unit,
wherein step (iii) is performed for at least two surfaces of the test piece by rotating the test piece by using a chucking unit that is capable of rotating the test piece so that the at least two surfaces are positioned at the detection unit.

14. The plastic identifying method according to claim 13, wherein step (iii) includes a step of irradiating infrared light of a predetermined wave number onto the test piece, and detecting the intensity of the infrared light that is totally reflected by the test piece.

15. The plastic identifying method according to claim 13, wherein step (iii) is performed by bringing the test piece into contact with the detection unit.

16. The plastic identifying method according to claim 15, wherein step (iii) is performed by bringing the test piece into contact with the detection unit after letting the test piece become stationary above the detection unit.

* * * * *